United States Patent [19]

Yoneta et al.

[11] Patent Number: 5,565,342
[45] Date of Patent: * Oct. 15, 1996

[54] PROCESS FOR PRODUCING POLYSACCHARIDE RON SUBSTANCE WITH A SYNTHETASE

[75] Inventors: Yasuo Yoneta; Hisao Kado; Suguru Takeo; Yutaka Mitani; Nobuhiro Watanabe, all of Yaizu, Japan

[73] Assignee: Sapporo Breweries Limited, Tokyo, Japan

[*] Notice: The portion of the term of this patent subsequent to Jul. 26, 2011, has been disclaimed.

[21] Appl. No.: 122,138

[22] Filed: Sep. 15, 1993

Related U.S. Application Data

[63] Continuation of Ser. No. 912,128, Jul. 9, 1992, abandoned, which is a continuation of Ser. No. 807,969, Dec. 11, 1991, abandoned, which is a continuation of Ser. No. 467,857, Jan. 22, 1990, abandoned.

[30] Foreign Application Priority Data

Feb. 8, 1989 [JP] Japan ..................... 1-29382

[51] Int. Cl.$^6$ .............. C12P 19/04; C12N 1/12; C12N 1/10; C07H 5/04
[52] U.S. Cl. ............. 435/101; 435/183; 435/252.1; 435/822; 536/55.1; 536/124
[58] Field of Search ........................... 435/101, 183, 435/822, 252.1; 536/55.1, 124

[56] References Cited

U.S. PATENT DOCUMENTS 4,762,825 8/1988 Takeo et al. ................. 514/54

FOREIGN PATENT DOCUMENTS

| 0087404 | 2/1983 | European Pat. Off. . |
| 0172559 | 8/1985 | European Pat. Off. . |
| 3224547 | 1/1984 | Germany . |

OTHER PUBLICATIONS

Chemical Abstracts, vol. 110, No. 1, Jan. 2, 1989, Columbus, Ohio, USA, Takeo Suguru et al., "Studies on an Antitumor Polysaccharide RBS Derived from Rice Bran. II. Preparation and General Properties of RON, an Active Fraction of RBS." p. 392, abstract No. 387w & Chem. Pharm. Bull. 1988, 36(9), 3609–13.

Marina E. Preobrazhenskaya et al, Studies on Some Biologically Active Dextrans, Carbohydrate Research, 66 (1978) pp. 213–223.

S. M. Navashin et al, Antitumor and Antibacterial Activity of Dextran LU–122 and Its Effect on Macrophage Activity, Curr. Chemother. Immunother., Proc. Int. Congr. Chemther., 12th, 1, pp. 190–192 (1982).

*Primary Examiner*—David M. Naff
*Assistant Examiner*—L. Blaine Lankford
*Attorney, Agent, or Firm*—Frishauf, Holtz, Goodman, Langer & Chick, P.C.

[57] ABSTRACT

A polysaccharide RON substance which has antitumor activity can be produced by fermenting sucrose with a synthetase. The synthetase can be isolated from Leuconostoc strains. Preferred strains of the microorganism are *Leuconostoc mesenteroides* FERM BP-2242, 2711, 2712, 2713, 2714, and 2670. The substance exhibits antitumor activity against syngenic tumor Meth A, a transplantable tumor in mice.

8 Claims, 3 Drawing Sheets

5,565,342

PROCESS FOR PRODUCING POLYSACCHARIDE RON SUBSTANCE WITH A SYNTHETASE

This application is a continuation of application Ser. No. 07/912,128 filed Jul. 9, 1992, (abandoned), which is a continuation of application Ser. No. 07/807,969 filed Dec. 11, 1991 (abandoned), which is a continuation of application Ser. No. 07/467,857 filed Jan. 22, 1990 (abandoned).

BACKGROUND OF THE INVENTION

1. Field of the Invention

The present invention relates to an enzyme having an action of synthesizing from sucrose a biologically active polysaccharide RON substance (hereinafter referred to as "RON substance" according to circumstances) having excellent antitumor activity, immunomodulating activity and host defense activity against infectious diseases, and a process for producing this RON substance by using this enzyme.

2. Description of the Related Art

The RON substance intended in the present invention and a process for extracting this RON substance from rice bran have already been disclosed in Japanese Patent Publication No. 62-7173 (which corresponds to U.S. Pat. No. 4,762,825).

According to this conventional process, the RON substance is extracted from rice bran and the extract is purified. Therefore, the quality of the starting material is unstable, and there are considerable dispersions of the physicochemical properties and biologically activities of the obtained substance. Moreover, the yield is low and many steps are required, and the conventional process involves the problem of long operation time and is economically disadvantageous.

SUMMARY OF THE INVENTION

Under this background, we made an extensive investigation with a view to overcoming the above-mentioned defects of the conventional techniques, and as the result, it was found that a microorganism belonging to the genus Leuconostoc produced extracellularly an enzyme capable of synthesizing the RON substance from sucrose, that is, the RON substance synthetase, and the RON substance having stable physicochemical properties and biological activities can be obtained in a high yield by treating sucrose with this enzyme. We have now completed the present invention based on this finding.

More specifically, in accordance with the present invention, there is provided a biologically active polysaccharide RON substance synthetase capable of forming a biologically active polysaccharide RON substance having the following properties by reaction on sucrose:

(1) Form: the substance is a white amorphous powder having no taste and no smell;

(2) Solubility: the substance is soluble in water but the solution becomes milky white and viscous when the concentration is elevated, the substance is soluble in formamide and dimethylsulfoxide but the substance is insoluble in alcohols, acetone, benzene, ethyl acetate, hexane, chloroform and carbon tetrachloride;

(3) pH of Aqueous Solution: the aqueous solution is neutral or weakly acidic;

(4) Constituent Saccharide: the substance is composed solely of glucose;

(5) Elementary Analysis Values: the substance comprises 44.0 to 45.0% of C and 6.1 to 6.3% of H;

(6) Structure: the substance is an α-1,6-glucan and containing a small amount of 3,6-branched side chains;

(7) Proteins: the substance contains almost no proteins;

(8) Molecular Weight: the substance does not permeate through a dialysis membrane and the molecular weight is presumed to be higher than 10,000 daltons;

(9) Specific Rotation: $[\alpha]_D^{25} = +190° \sim +220°$ (C=0.5, formamide);

(10) Color Reaction: the substance is positive to anthrone sulfuric acid reaction and phenol sulfuric acid reaction but negative to the biurette reaction, the Lowry-Folin reaction, the Elson-Morgan reaction and the iodine reaction;

(11) Melting Point: the substance has no definite melting point;

(12) Ultraviolet Absorption Spectrum: the substance has no characteristic absorption;

(13) Infrared Absorption Spectrum: the substance shows a characteristic absorption of α-glucan;

(14) $^{13}$C-NMR Spectrum: the substance shows characteristic chemical shift values of α-1,6-glucan in the main signals; and

(15) Biological Activity: the substance has an antitumor activity.

Furthermore, in accordance with the present invention, there is provided a process for producing the RON substance, which comprises treating sucrose with the above-mentioned enzyme to form the above-mentioned biologically active polysaccharide RON substance and collecting the said substance.

DETAILED DESCRIPTION OF THE PREFERRED EMBODIMENTS

Figure 1:
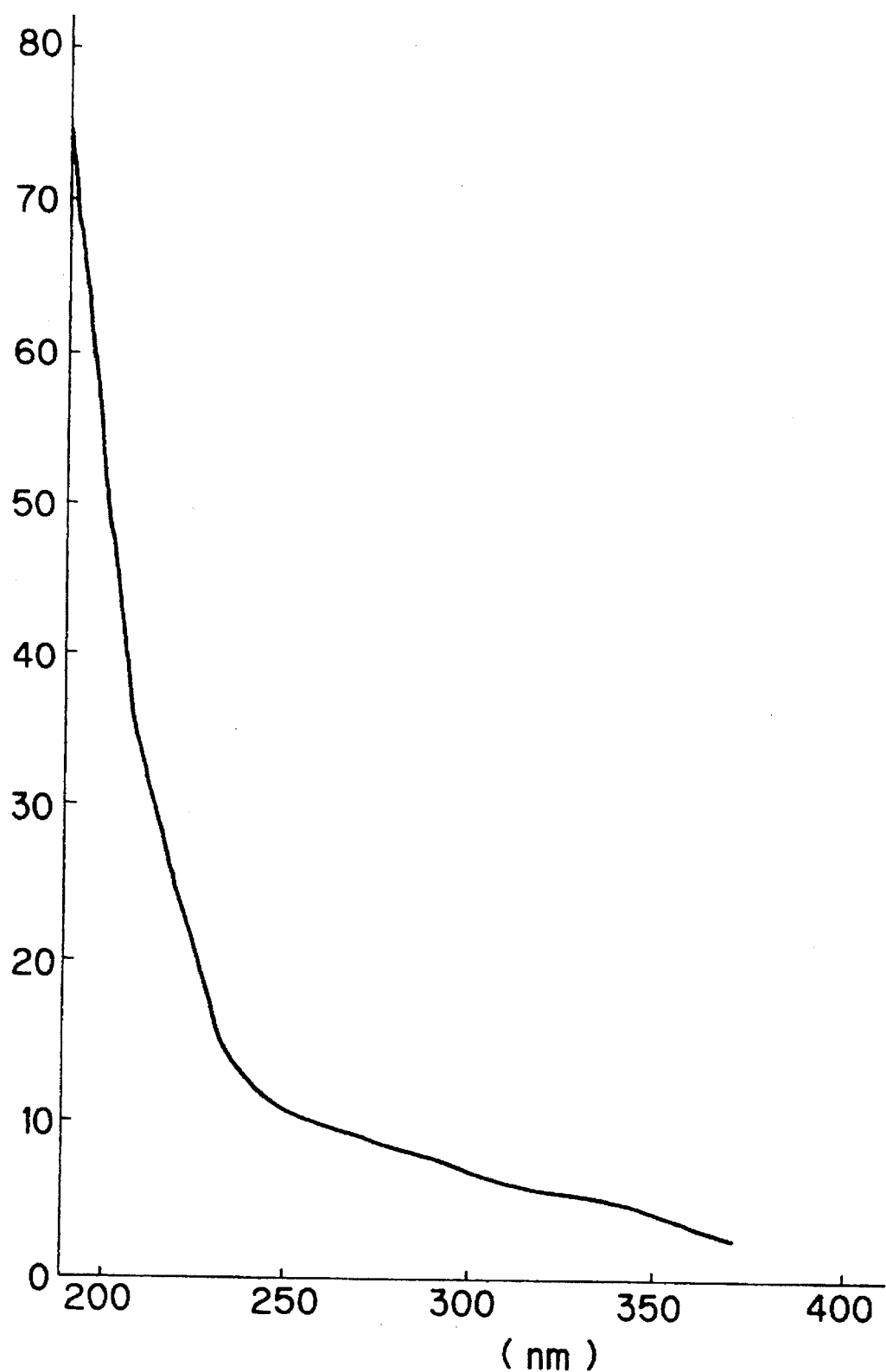
FIG. 1 shows the ultraviolet absorption spectrum of the RON substance obtained by the present invention.

The biologically active polysaccharide RON substance synthetase of the present invention can be produced according to the following process.

A microorganism capable of producing the RON substance synthetase forming the RON substance having the above-mentioned properties is cultivated in a culture medium, the RON substance synthetase is accumulated in the culture broth and then the synthetase is collected. As the microorganisms capable of producing the present enzyme, there can be mentioned microorganisms belonging to the genus Leuconostoc. As specific examples of the microorganism capable of producing the RON substance synthetase, there can be mentioned *Leuconostoc mesenteroides* subsp. *dextranicum*, strain BL-75 and strain 46-1 isolated from rice bran etc. The microbiological characteristics of these strains are as follows.

Strain BL-75

Gram stain: +

Morphological characteristics: spherical to ellipsoidal, 0.4 to 0.7 μm, chain of 3 to 4 cocci, formation of cluster Catalase reaction: −

Oxidase reaction: −

Free oxygen demand: facultative anaerobic

Decomposition of arginine: −

Lactic acid fermentation: hetero type, D-lactic acid

Production of acid from carbohydrates:

arabinose: − fructose: + galactose: + glucose: + lactose: + mannose: + trehalose: +

Hydrolysis of esculin: +

Production of dextran: +

Growth in the presence of NaCl:

3.0% NaCl: +

6.5% NaCl: −

Growth at different initial pH values:

pH 4.8: − pH 6.5: +

Final pH in glucose medium: 4.3

Strain 46-1

Gram stain: +

Morphological characteristic: spherical to ellipsoidal, 0.4 to 0.6 μm, pair and short chain Catalase reaction: −

Oxidase reaction: −

Free oxygen damand: facultative anaerobic

Decomposition of arginine: −

Lactic acid fermentation: hetero type, D-lactic acid

Production of acid from carbohydrates:

arabinose: − fructose: + galactose: + glucose: + lactose: + mannose: + trehalose: +

Hydrolysis of esculin: +

Production of dextran: +

Growth in the presence of NaCl:

3.0% NaCl: +

6.5% NaCl: −

Growth at different initial pH values:

pH 4.8: ± pH 6.5: +

Final pH in glucose medium: 4.1

In view of the foregoing, the mycological properties of both strains are summarized as follows.

1. Both strains are positive to the Gram stain and are facultative anaerobic.

2. The morphological characteristic is in a chain of spherical to ellipsoidal cocci.

3. Both strains are positive to the production of acid from carbohydrates except arabinose.

4. The lactic acid fermentation is of the hetero type, and only the D-form of lactic acid is formed.

5. Both strains are negative to the decomposition of arginine.

With reference to Bergey's Manual of Determinative Bacteriology, 8th edition, it was judged that the strain BL-75 belonged to the genus Leuconostoc, and since the strain was positive to the production of dextran and negative to the production of an acid from arabinose and the strain did not grow in the presence of 6.5% NaCl, therefore the strain BL-75 was identified as a strain of *Leuconostoc dextranicum* and deposited as FERM BP-2242 in the Fermentation Research Institute, Agency of Industrial Science and Technology, Ministry of International Trade and Industry.

Afterward, we learned by reading afterdescribed new hand books that the name of the species of *Leuconostoc dextranicum* was changed. Accordingly, the strain LB-75 and the strain 46-1 found afterward, were investigated again with reference to Bergey's Manual of Systematic Bacteriology, Vol. 2, 9th edition (1986) and Methods in Microbiology, Vol. 16, pages 147 and 148 (1984). As the result, both strains were identified as the strains of *Leuconostoc mesenteroides* subsp. *dextranicum*. Accordingly, we changed the name of strain BL-75 to *Leuconostoc mesenteroides* subsp. *dextranicum*, BL-75, and strain 16-1 was named *Leuconostoc mesenteroides* subsp. *dextranium*, 46-1 and the latter was also deposited as FERM BP-2670 with Fermentation Research Institute, Agency of Industrial Science and Technology, Ministry of International Trade and Industry.

We further searched for the RON substance-producing microorganisms, and it was found that some known strains had an activity of producing the RON substance as well as the strains BL-75 and 46-1. Namely, *Leuconostoc mesenteroides* subsp. *dextranicum*, strain NCFB 517 (FERM BP-2711), strain NCFB 531 (FERM BP-2712), strain NCFB 861 (FERM BP-2713), strain NCFB 864 (FERM BP-2714), strain NCFB 880 (FERM BP-2715), strain ATCC 1956 and strain IFO 3349 were found to be RON substance producers.

Accordingly, any of the microorganisms belonging to the genus Leuconostoc and being capable of producing the RON substance can be utilized for the production of the RON substance of the present invention.

Culture of the microorganism capable of producing the enzyme having a RON substance-producing activity is, in principle, carried out according to an ordinary microorganism-culture method. Since the microorganism belonging to the genus Leuconostoc is facultative anaerobic and it demands no oxygen, a stationary culture using a liquid medium or gently agitating culture to unify the temperature distribution is generally advantageously adopted.

In the culture medium, sucrose should be indispensably contained as the carbon source for the production of a RON substance-producing enzyme. Any of synthetic culture media, semi-synthetic culture media and natural media can be used, so far as other carbon source, a nitrogen source, an inorganic substance and other nutrient sources that can be utilized by the above-mentioned enzyme-producing microorganism are contained in addition to sucrose.

Any of crude and refined products of sucrose can be optionally used. For example, first-class white refined sugar, molasses or sucrose of the reagent grade can be used. A higher sucrose concentration gives a higher productivity of the present enzyme but simultaneously, because it gives a higher concentration of the formed RON substance and a removal of cells becomes difficult. Accordingly, a sucrose concentration of about 1 to about 3% is generally preferable. As the nitrogen source, there can be used yeast extract, peptone, gluten meal, soybean meal, corn steep liquor, dry yeast, meat extract, ammonium sulfate and urea. As the inorganic substance, there can be used phosphoric acid salts and salts of metals such as magnesium, manganese, iron, cobalt and sodium can be appropriately added. Since the pH value has influences on the formation of the present enzyme, it is preferred that a phosphoric acid salt is added in an amount of about 1 to about 3% in order to increase the buffer capacity of the culture medium.

The incubation temperature may be one for mesophiles, therefore, it is generally 15° to 45° C., preferably 20° to 30° C. The incubation time is generally 10 to 30 hours, after the formation of the present enzyme reaches the climax, the incubation is stopped.

Since the present enzyme is accumulated in the cells and the culture medium, the present enzyme can be collected from the cells gathered by the centrifugal separation, or can be collected from the supernatant left after the removal of the cells. Incidentally, the culture broth is itself or the above-mentioned cells or supernatant can be used as the crude enzyme for the production of the RON substance. When the present enzyme is recovered from the cells, there can be adopted a method in which the present enzyme is solubilized by appropriate means, for example, extraction with a surface active agent or sonification of cells, and insoluble substances are removed by such method as centrifugal separation. However, since recovery from the supernatant is easier, the present enzyme is generally recovered from the supernatant.

The purification of the present enzyme can be performed by means customarily adopted for the purification of enzymes, such as precipitation with an organic solvent, salting-out, various chromatographies (ion exchange chromatography, gel filtration chromatography, hydrophobic chromatography, affinity chromatography and hydroxyapatite chromatography) and ultrafiltration. The present enzyme can be sufficiently purified by the removal of low-molecular-weight components (having a molecular weight lower than 30,000 daltons) by ultrafiltration.

The properties of the RON substance-forming enzyme of the present invention will now be described. The enzyme obtained in Example 1 given hereinafter was used as the standard substance of the present enzyme. The enzyme activity was measured according to the following method.

Measurement of Enzyme Activity

The enzyme activity was determined by measuring the amount of fructose set free simultaneously with the formation of the RON substance.

A substrate solution comprising sucrose (60 w/v %) and an acetate buffer (0.3M, pH 5.5), which was warmed to 30° C. in advance, was mixed with an enzyme solution (0.5 to 1 U/ml) warmed to 30° C. in an amount 4 times the amount of the substrate solution, and the mixture was sufficiently stirred and the reaction was carried out at 30° C. for 30 minutes. To the reaction mixture a 40 mM of NaOH solution was added in an amount 5 times of the amount of the reaction mixture to stop the reaction. The reaction-stopped mixture was appropriately diluted and reducing sugar was determined as fructose by the Somogyi method [M. Somogyi, J. Biol. Chem., 160, 61 (1945)]. As the control, reducing sugar in the enzyme reaction-stopped mixture treated in the same manner without adding sucrose was determined as fructose, and correction was carried out. The quantity of sucrose participating in the reaction was determined from the quantity of fructose. The activity of the RON substance synthetase is expressed in such a manner that 1 unit is the amount of the enzyme converting 1 µmole of sucrose to the RON substance in 1 minute under the above-mentioned conditions.

Properties of Enzyme (a) Mode of Action

The enzyme decomposes 1 mole of sucrose to form 1 mole of fructose, and simultaneously, the enzyme transfers the glucose portion to the RON substance acting as a receptor.

(b) Optimum pH

The relative activities at different pH values were determined at 30° C. using different buffer solutions. It was found that an optimum pH value for the present enzyme is about 5.5.

(c) Stable pH Range

The relative residual activities at different pH values were measured after standing the enzyme solution at 25° C. for 18 hours in each pH value. It was found that the present enzyme is stable in buffer solutions having a pH value of from 4.5 to 7.0.

When the present enzyme solution was saturated with toluene at a pH value of 5.5 and stored in a cold state (4° to 6° C.), the enzyme was stable for 2 months.

(d) Substrate Specificity

Formation of the RON substance from glucose, fructose, maltose and isomaltose is not observed, but the enzyme reacts only with sucrose to form the RON substance.

(e) Optimum Temperature

According to the above-mentioned method, the activity of the enzyme were measured at various temperatures, and relative activities at the respective temperatures were determined. It was found that the optimum temperature of the present enzyme is about 40° C. at pH 5.5.

(f) Stable Temperature Range

The relative residual activities at different temperatures were determined after standing the enzyme solution for 30 minutes at pH 5.5. It was found that the present enzyme is stable at temperatures lower than 40° C.

(g) Inhibition and Activation

The relative activities at the addition of the different metal chlorides in the final concentration of 1 mM were determined by the standard method. The relative value was expressed in percent comparing with the activity without addition of any metal chloride. The obtained results are shown in Table I.

TABLE I

| Metal Salt | Relative Activity (%) |
| --- | --- |
| not added | 100 |
| $MgCl_2$ | 78 |
| $CaCl_2$ | 110 |
| $MnCl_2$ | 75 |
| $FeCl_2$ | 103 |
| $FeCl_3$ | 82 |
| $CoCl_2$ | 95 |
| $NiCl_2$ | 98 |
| $CuCl_2$ | 50 |
| $ZnCl_2$ | 93 |

Table I show that the enzyme is slightly activated by Ca salt but is inhibited by Cu salt.

When the present enzyme is subjected to a gel filtration, the enzyme is eluted at a void volume of the column (Toyopearl HW-75®) having an exclusion limit at molecular weight of 10,000,000 daltons. However, the RON substance is simultaneously eluted in a same position. Therefore it is presumed that the present enzyme has a high affinity with the RON substance and is bound thereto. It has been confirmed that when the present enzyme is separated from the polysaccharide RON substance, the activity of the enzyme becomes unstable. Practically the present enzyme can be sufficiently purified according to the above-mentioned method, but in this case, the present enzyme is not purified to a single protein judged by an electrophoresis. Therefore, the molecular weight, elementary analysis values, crystal structure and the like of the present catalyst have not been clarified.

The present enzyme has an action of decomposing sucrose to form the biologically active polysaccharide RON substance. Accordingly, the RON substance can be produced using the present enzyme.

The above-mentioned (not completely purified) enzyme of the present invention can be used sufficiently as the RON substance-synthesizing enzyme. Use of sucrose having a higher purity is advantageous for the purification of the RON substance, but practically, commercially available white sugar is satisfactory. When the sucrose concentration in the reaction mixture is higher, the amount of the formed RON substance increases, but the time required for the reaction becomes long. Accordingly, the reaction is generally carried out at a sucrose concentration of 5 to 30%, preferably 10 to 20%.

When the enzyme concentration in the reaction mixture is higher, the time required for the reaction becomes short, but in the case where the sucrose concentration is the same, the amount of the formed RON substance is not different. Therefore, the reaction is generally carried out at an enzyme concentration of 0.2 to 2 U/ml, preferably 0.5 to 1 U/ml.

The pH value of the reaction mixture may be within the stable pH range of the enzyme, but since the highest efficiency is obtained if the reaction is carried out at the optimum pH value of the enzyme, the pH value is preferably adjusted to about 5.5. The pH value is not changed by the enzyme reaction, and if a phosphate or acetate buffer solution is used, the pH value of the reaction mixture can be easily maintained.

The reaction temperature may be within the stable temperature range, but since the efficiency of the enzyme reaction is higher as the temperature is higher, the enzyme reaction is preferred to be carried out at about 30° C.

The reaction time depends on the sucrose concentration, the enzyme concentration, the reaction temperature and the pH value of the reaction mixture. However, it might be recommended that the practical reaction time is preferably 6 to 7 hours.

After the reaction, the formed RON substance can be purified by organic solvent precipitation using a water-soluble polar organic solvent. Organic solvents customarily used for the purification of polysaccharides, for example, methanol, ethanol and acetone, can be used. The organic solvent is added to the reaction mixture until the RON substance is precipitated enough. However, in order to prevent a contamination of impurities in the reaction mixture, such as sucrose, fructose and a buffer agent, it is preferred that the organic solvent should be carefully added with stirring so that the final concentration is 40 to 60%, preferably 43 to 48%. The formed precipitate can be recovered by filtration or centrifugation, but the recovery by decantation is simple and advantageous. In general, it is preferred that this operation should be repeated several times to remove the impurities. After the RON substance recovered as the precipitate is dissolved in water, and the solution is subjected to freeze drying or spray drying. It is also available that the solution is gradually added into a polar organic solvent and the precipitation is dried under reduced pressure in the dehydrated state. The RON substance is recovered in the form of a white powder. Furthermore, the RON substance can be prepared at a higher efficiency by a bioreactor utilizing the RON substance-synthesizing enzyme.

Since the enzyme having a fixed titer is used in the process for producing the RON substance according to the present invention, it is possible to carry out the production of the RON substance under optimum conditions. Therefore, a product having a uniform quality can be obtained in a short time. Furthermore, since the RON substance-producing microorganism is not directly used for the production of the RON substance, starting sucrose is not consumed for the growth of the microorganism. Accordingly, the efficiency of utilization of the starting material is high. Moreover, because there is not a fear of decomposition of the RON substance formed by the enzyme, the yield is higher and purification is easier than that obtained by the fermentative production.

Figure 2:
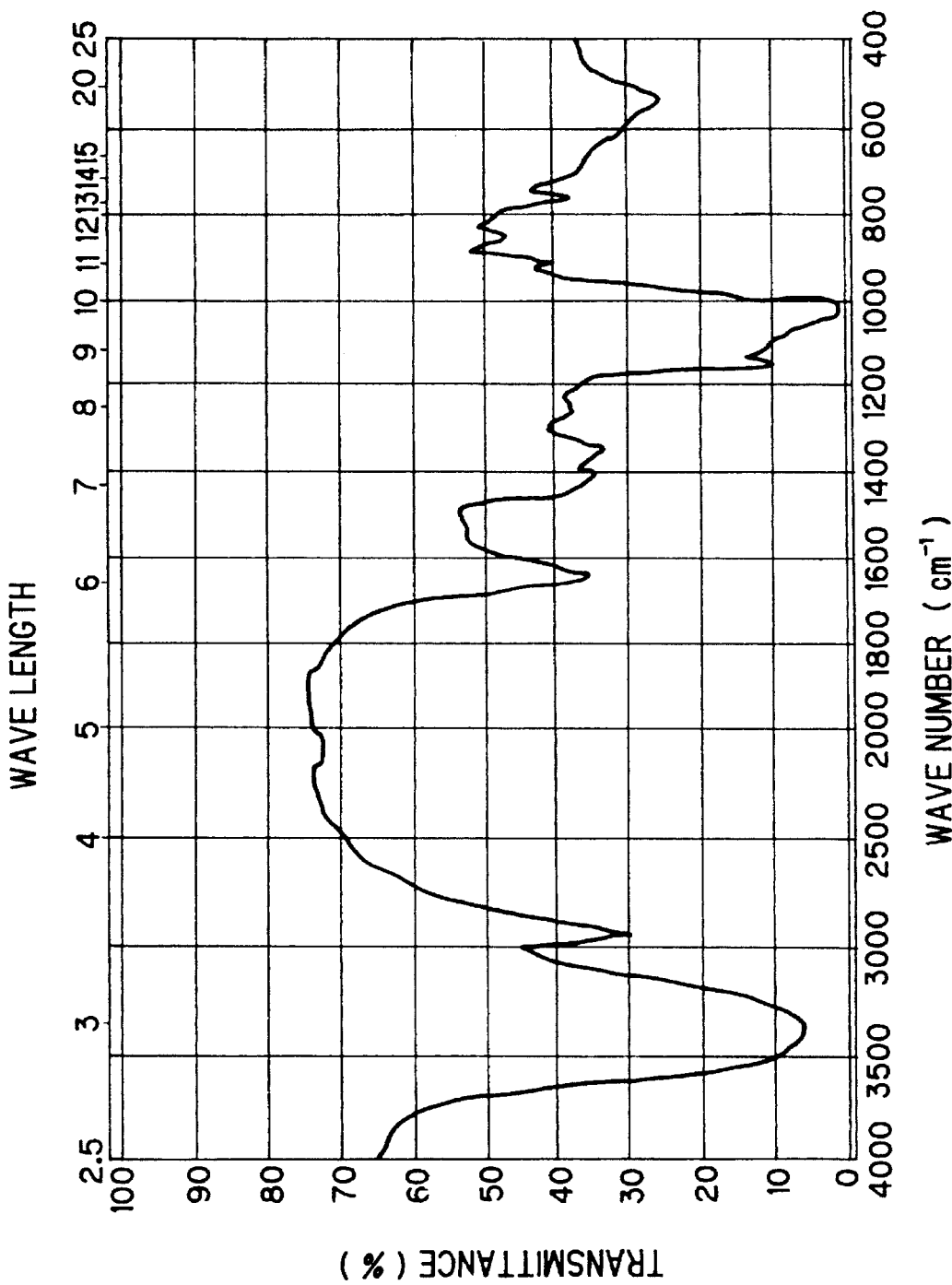
FIG. 2 shows the infrared absorption spectrum of the RON substance.
Figure 3:
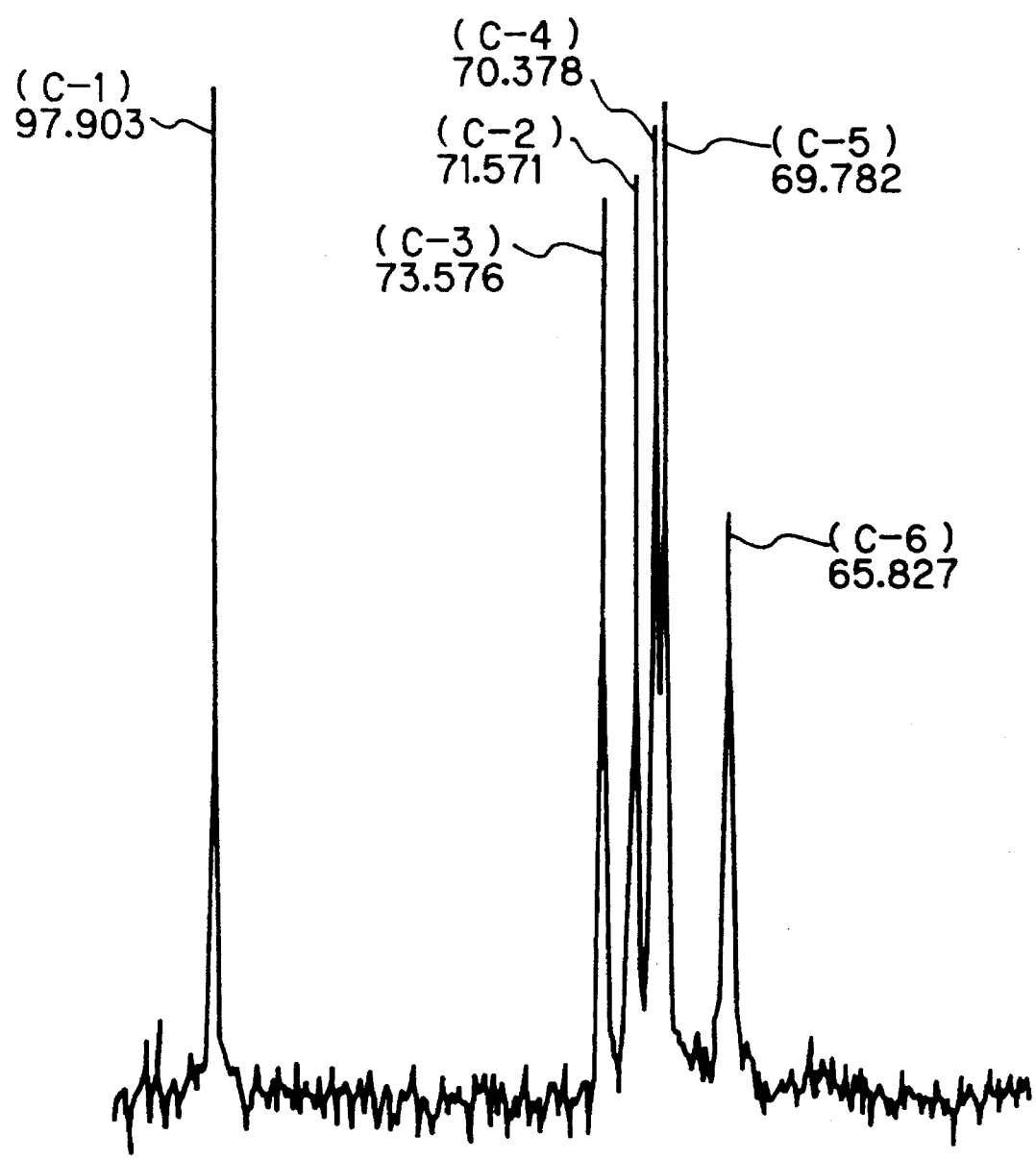
FIG. 3 shows the $^{13}$C-NMR spectrum of the RON substance.

The properties of the so-obtained biologically active polysaccharide RON substance are as follows:

(1) Form: the substance is a white amorphous powder having no taste and no smell;

(2) Solubility: the substance is soluble in water but the solution becomes milky white and viscous when the concentration is elevated, the substance is soluble in formamide and dimethylsulfoxide but the substance is insoluble in alcohols, acetone, benzene, ethyl acetate, hexane, chloroform and carbon tetrachloride;

(3) pH of Aqueous Solution: the aqueous solution is neutral or weakly acidic;

(4) Constituent Saccharide: the substance is composed solely of glucose;

(5) Elementary Analysis Values: the substance comprises 44.0 to 45.0% of C and 6.1 to 6.3% of H;

(6) Structure: the substance is an α-1,6-glucan and containing a small amount of 3,6-branched side chains;

(7) Proteins: the substance hardly contains proteins;

(8) Molecular Weight: the substance does not permeate through a dialysis membrane and the molecular weight is presumed to be higher than 10,000 daltons, and for example according to the gel permeation method using Sepharose 2B®, it is presumed that the molecular weight which was obtained according to later-described Example 2 is higher than 20,000,000 daltons;

(9) Specific Rotation: $[\alpha]_D^{25}=+190° \sim 220°$ (C=0.5, formamide);

(10) Color Reaction: the substance is positive to anthrone sulfuric acid reaction and phenol sulfuric acid reaction but negative to biurette reaction, the Lowry-Folin reaction, the Elson-Morgan reaction and iodine reaction;

(11) Melting Point: the substance has no definite melting point;

(12) Ultraviolet Absorption Spectrum: the substance has no characteristic absorption as shown in FIG. 1;

(13) Infrared Absorption Spectrum: the substance shows a characteristic absorption of α-glucan, as shown in FIG. 2;

(14) $^{13}$C-NMR Spectrum: the substance shows a characteristic chemical shift values of α-1,6-glucan at the main peak, as shown in FIG. 3; and

(15) Biological Activity: the substance has an antitumor activity.

It was found that the RON substance obtained according to the present invention had various biological activities such as an antitumor activity, an immunomodulating activity and a host defense activity against infectious diseases. The methods for testing these biological activities and the results obtained when the RON substance obtained in Example 2 given hereinafter was administered are described in detail.

(1) Antitumor Activities (a) Effect of Intraperitoneal Administration of the RON Substance against Syngeneic Tumor Meth-A To the peritoneal cavities of 6-weeks-old female BALB/C-CRJ mice having an average body weight of 20 g, Meth-A tumor cells subcultured in the peritoneal cavities of syngeneic mice were transplanted at a rate of 1×10$^5$ cells per mouse. The mice were divided into one control group consisting of 20 mice and three test groups, each consisting of 10 mice. Continuously for 5 days from the day subsequent to the transplantation of the tumor cells, 0.1 ml each of physiological saline solutions containing 10 mg, 30 mg and 100 mg of RON per kg of the body weight of one mouse were administered intraperitoneal by cavities to the mice of test groups, respectively, and only a physiological saline solution alone was similarly administered to the mice of the control group. Then, the survival days were observed, and the prolongation of life was calculated according to the following formula:

$$\text{Prolongation of life (\%)} = \frac{\text{average survival time (days) for test group}}{\text{average survival time (days) for control group}} \times 100$$

(b) Effect of Oral Administration of the RON Substance against Syngeneic Tumor Meth-A In the axillary regions of 6 week-old female BALB/C-CRJ mice having an average body weight of 20 g, Meth-A tumor cells were subcutaneously transplanted at a rate of 6×10$^4$ cells per mouse. The mice were divided into one control group consisting of 20 mice and three test groups, each consisting of 10 mice. Continuously for 10 days from the day subsequent to transplantation of the tumor cells, 0.2 ml each of physiological saline solutions containing 10, 30 and 100 mg of the RON substance per kg of the body weight of one mouse were administered orally by using an oral sonde. Only a physiological saline was similarly administered to the mice of the control group. After 35 days from the transplantation of the tumor cells, each mouse was killed, and the propagated tumor was cut out and the weight was measured. The inhibition ratio was calculated according to the following formula:

$$\text{Inhibition ratio (\%)} = \left(1 - \frac{\text{average tumor weight in test group}}{\text{average tumor weight in control group}}\right) \times 100$$

The antitumor activities of the RON substance tested according to the above-mentioned methods (a) and (b) are shown in Table II.

TABLE II

| Sample | Dose (mg/kg) | Intraperitoneal Administration (a) | | Oral Administration (b) | |
|---|---|---|---|---|---|
| | | average survival time (days) | prolongation of life (%) | average tumor weight (g) | inhibition ratio (%) |
| control (saline) | — | 18.7 | — | 10.87 | — |
| RON substance | 10 | 28.1 | 150 | 6.52 | 40 |
| RON substance | 30 | >37.4 | >200 | 4.57 | 58 |
| RON substance | 100 | 29.0 | 155 | 5.44 | 50 |

From the results shown in the Table II, it can be seen that the RON substance exhibits a strong antitumor activity with the optimum dose of about 30 mg/kg both in the intraperitoneal and in the oral administration.

Furthermore, it was confirmed that when the RON substance is intraperitoneally or orally administered at a dose of 10 to 100 mg/kg, activities corresponding to a tumor inhibition ratio of 30 to 70% is attained for the murine syngeneic tumors Lewis lung carcinoma, the Melanoma B-16, and allogeneic tumors Sarcoma-180 and Ehrlich ascites tumor. Moreover, it was confirmed that when the RON substance is administered to mice in combination with an appropriate primer, the cytotoxicity to L-929 cells and the necrotic activity to Meth-A solid tumor are induced in the serum, and a tumor necrosis factor is self-induced in the living body of a tumor-bearing mice. In view of the fact that the RON substance has no toxicity at all as described hereinafter, it is considered that the RON substance can be a very effective antitumor agent.

(2) Immunomodulating Activities (a) Carbon Clearance Test (CCT)

This test is used to examine the effect of enhancing the phagocytic activity of the macrophage. A physiological saline solution containing the RON substance dissolved therein was intraperitoneally administered for 2 days into one group of six 4-week- old female ICR-CRJ mice having an average body weight of 20 g (only a physiological saline was administered to the control group), and on the third day, 0.25 ml of a carbon solution [prepared by diluting a back ink (Fount India® supplied by Perikan Co.) 5 times with a physiological saline solution] was injected into the tail vein of the mouse. Just after the injection and after 10 minutes, 0.025 ml of blood was collected from the venous plexus of the retro-orbit of the mice and suspended and dissolved in 3.5 ml of a 0.01M solution of sodium carbonate. The absorbance (OD$_{650}$) at 650 nm was measured and the reduction ratio of the carbon concentration in blood was examined. The effect was expressed by the phagocytic index represented by the following formula:

$$\text{Phagocytic index } (K) = \frac{\log C_1 - \log C_2}{T_2 - T_1}$$

wherein $C_1$ represents OD$_{650}$ at $T_1$ and $C_2$ represents OD$_{650}$ at $T_2$.

In case of tumor-bearing mice, 7 days before initiation of administration of the RON substance, $1 \times 10^7$ of Sarcoma-180 cells were transplanted in the muscle of the hind leg of each mouse, and the test was similarly carried out. The obtained results are shown in Table III. It was found that in case of both normal mice and tumor-bearing mice, the function of the reticuloendothelial system of the mice is enhanced by the administration of 10 to 100 mg/kg, especially 30 mg/kg, of the RON substance.

TABLE III

| Sample | Dose (mg/kg) | Normal Mice Phagocytic index | relative value (%) | Tumor-Bearing Mice phagocytic index | relative value (%) |
| --- | --- | --- | --- | --- | --- |
| control (saline) | — | $40.8 \times 10^{-3}$ | 100 | $100 \times 10^{-3}$ | 100 |
| RON substance | 10 | $53.0 \times 10^{-3}$ | 130 | $127 \times 10^{-3}$ | 118 |
| RON substance | 30 | $85.7 \times 10^{-3}$ | 210 | $162 \times 10^{-3}$ | 150 |
| RON substance | 100 | $74.3 \times 10^{-3}$ | 182 | $143 \times 10^{-3}$ | 132 |

(b) Plaque-Forming Cell Test (PFC)

This test is used to examine the effect of enhancing the antibody-producing ability by activation of B cells of the host among the immunomodulating activities.

A physiological saline solution containing the RON substance was continuously administered for 3 days intraperitoneally cavities to one group of six 4-week-old female ICR-CRJ mice having an average body weight of 20 g (only a physiological saline was administered to the control group). On the 4th day and 11th day, $4 \times 10^6$ of sheep erythrocytes were injected into the tail vein, and after 4 days, the plaque-forming ability of the mouse spleen cells was determined according to the Cunningham method.

The obtained results are shown in Table IV. It is seen that the antibody-producing ability is highly enhanced by the administration of 10 to 100 mg/kg of the RON substance.

TABLE IV

| Sample | Dose (mg/kg) | Sensitization on 4th Day number of plaques per spleen | relative value (%) | Sensitization on 11th Day number of plaques per spleen | relative value (%) |
| --- | --- | --- | --- | --- | --- |
| control (saline) | — | $2.7 \times 10^4$ | 100 | $2.5 \times 10^4$ | 100 |
| RON substance | 10 | $3.8 \times 10^4$ | 147 | $5.3 \times 10^4$ | 212 |
| RON substance | 30 | $5.8 \times 10^4$ | 215 | $6.8 \times 10^4$ | 272 |
| RON substance | 100 | $5.6 \times 10^4$ | 208 | $6.7 \times 10^4$ | 268 |

(c) Delayed Type Hypersensitivity Reaction (DHR)

This test is used to examine the effect of enhancing the cell-mediated immunity action by the activation of T cells of the host among the immunomodulating activities.

A physiological saline solution containing the RON substance was orally administered to one group of six 8week-old female ICR-CRJ mice having an average body weight of 27 g (only a physiological saline was administered to the control group). On the 4th day after the initiation of administration, a 5% ethanol solution of picryl chloride was coated on the abdominal region which had been shaved to effect the primary sensitization. On the 11th day, a 1% olive oil solution of picryl chloride was coated on the front and back sides of both the ears of each mouse to effect the secondary sensitization. After 24 hours, the ear thickness was measured by a gauge, and the increase of the ear thickness was determined from the difference between the ear thickness before and after the coating. In case of tumor-bearing mice, $1 \times 10^5$ of Sarcoma 180 ascitic tumor cells were transplanted into the peritoneal cavity of the mouse one day before the administration. Then, the test was similarly carried out.

The obtained results are shown in Table V. It is seen that in case of both normal mice and tumor-bearing mice, the cell-mediated immunity action is highly enhanced by the oral administration of 30 to 500 mg/kg of the RON substance.

TABLE V

| Sample | Dose (mg/kg) | Normal Mice increase of ear thickness (μm) | relative value (%) | Tumor-Bearing Mice increase of ear thickness (μm) | relative value (%) |
| --- | --- | --- | --- | --- | --- |
| control (saline) | — | 30.2 | 100 | 10.3 | 100 |
| RON substance | 30 | 63.4 | 210 | 22.1 | 215 |
| RON substance | 100 | 71.0 | 235 | 23.2 | 225 |
| RON substance | 500 | 55.3 | 183 | 21.3 | 207 |

From the results of the immunity action tests (a), (b) and (c), it is seen that various immunity actions in mice having different mechanisms can be conspicuously enhanced by the RON substance. Since an immunomodulating agent is generally used when the immunological competence of a living body is reduced or the foreign antigen-recognizing function is poor, it is expected that the RON substance will be effectively used as a therapeutic agent, adjuvant therapeutic agent, combined therapeutic agent, preventing agent or recuperation-accelerating agent after the operation against bacterial and virus infectious diseases and malignant tumors. In addition to the above-mentioned immunity activating and recovering actions, the immunomodulating agent exerts a function of normalizing an abnormally enhanced immunoreaction in a living body, and it is considered that the RON substance will be applied to self-immunity diseases such as rheumatism, collagen diseases and allergic diseases.

(3) Host Defense Activity

In general, a living body has a sufficient defense activity against the invasion of foreign bacteria. It is known that in the cancer-bearing state, especially at the later stage of cancer, the defense action is drastically reduced and a serious damage is incurred even by non-pathogenic bacteria ordinarily symbiotic with the host.

Accordingly, in order to examine whether or not the RON substance can enhance the defense activity of the host against these bacterial infectious diseases, the effect of the RON substance on the infection with *Escherichia coli* and *Listeria monocytogenes* was examined.

A physiological saline solution containing 10 to 100 mg/kg of the RON substance was subcutaneously administered to the backs of one group of twenty 7-week-old female ICR-CRJ mice having an average body weight of 26 g (only physiological saline was administered to the control group) once one day before the infection with the bacteria and once one day after the infection with the bacteria. In case of *Escherichia coli*, $2\times10^7$ of cells were transplanted subcutaneously on the back, and in case of *Listeria monocytogenes*, $2\times10^7$ of cells were transplanted intraperitoneally. Then, the mice were observed for 1 week, and the number of survived mice was countered and the protective effect was calculated according to the following formula:

$$\text{Protective effect (\%)} = \frac{\text{(number of survival mice in test group)} - \text{(number of survival mice in control group)}}{\text{number of mice in one group}} \times 100$$

The obtained results are shown in Table VI. It is seen that if 10 to 100 mg/kg of the RON substance is administered before the infection with *Escherichia coli*, a very strong defense activity against the infection with *Escherichia coli* can be attained, and a significant effect of enhancing the defense activity against the infection with *Listeria monocytogenes*. In case of the administration after the infection, the RON substance has a significant therapeutic effect against both the infectious bacteria.

In view of the fact that the RON substance has no toxicity as illustrated hereinafter, it is considered that the RON substance can be a very useful host defense agent against infectious diseases.

against L-929 cells of resident peritoneal macrophages of a mouse. Moreover, the RON substance has an immunity activating ability and a function of enhancing a production of a cytokine such as interferon, and therefore, it is expected that the RON substance will exert preventive and therapeutic effects against virus diseases such as herpes, influenza and AIDS. Still further, it is considered that the RON substance will be useful as a preventive and therapeutic agent against hepatitis such as chronic hepatitis and liver diseases.

Since the RON substance can be orally or non-orally administered, it is expected that the RON substance will be effectively used as an antitumor agent, immunomodulating agent or preventive or therapeutic agent against infectious diseases.

In the practical production of medicines, the RON substance is combined with an excipient (such as water, physiological saline, polyethylene glycol, glycerol, starch, dextrin or lactose) and formed into a liquid preparation, a pill, a tablet, a powder or a suppository.

The RON substance has no toxicity, shows various biological activities valuable for the maintenance of health by oral administration, has no taste or smell and can be easily processed, therefore the RON substance can be used as a food or drink for prevention of diseases or maintenance of health or as an additive to foods or drinks in addition to medicines as mentioned above.

The RON substance of the present invention includes a macromolecule having a molecular weight higher than 20,000,000 daltons which obtained following Example 2, but it was found that a low-molecular-weight product

TABLE VI

| Infectious Bacterium | Sample | Dose (mg/kg) | One Day before Infection | | One Day after Infection | |
|---|---|---|---|---|---|---|
| | | | number of survival mice | Protective effect (%) | number of survival mice | protective effect (%) |
| *Escherichia coli**  | control (saline) | — | 0 | — | 0 | — |
| " | RON substance | 10 | 15 | 75 | 13 | 65 |
| " | RON substance | 30 | 17 | 85 | 16 | 80 |
| " | RON substance | 100 | 17 | 85 | 15 | 75 |
| *Listeria monocytogenese*** | control (saline) | — | 0 | — | 0 | — |
| *Listeria monocytogenese*** | RON substance | 10 | 9 | 45 | 9 | 45 |
| *Listeria monocytogenese*** | RON substance | 30 | 14 | 70 | 11 | 55 |
| *Listeria monocytogenese*** | RON substance | 100 | 13 | 65 | 10 | 50 |

Note
**Escherichia coli* SB-001
***Listeria monocytogenes* SB-010

The acute toxicity of the RON substance will now be described. The RON substance was orally administered to one group of ten 5-week-old male SD-CRJ rats having a body weight of 120 to 150 g at a dose of 15 g/kg, which is a physical administration limit dose, and the rats were observed. None of the rats died, and the increase of the body weight was not different from that in the control group and no abnormality was observed in both appearance and necropsy. Accordingly, it is judged that $LD_{50}$ is larger than 15 g/kg and the RON substance has no acute toxicity.

Furthermore, the RON substance has functions of enhancing the cytotoxicity of natural killer cells derived from spleen cells of rats and activating the cytotoxic activity formed by lowering the molecular weight of the RON substance to a certain level by acid hydrolysis or the like has biological activities comparable to those of the original macromolecular RON substance. More specifically, when the RON substance was hydrolyzed in a sulfuric acid/formic acid solution having a concentration of 0.5 to 5%, preferably 1 to 3%, at 30° to 70° C., preferably 50° to 60° C., for 2 to 24 hours, preferably 3 to 6 hours, then the hydrolyzed liquid was neutralized with barium carbonate. The supernatant was recovered by centrifugal separation, and the supernatant was concentrated and subjected to gel filtration in a column of Sepharose CL-2B® or Sephadex G-200®, and several fractions differing in the molecular weight were collected and the biological activities of the respective fractions are examined. It is seen that fractions having a molecular weight higher than about 10,000 daltons have activities comparable to those of the original macro-molecular RON substance.

The RON substance has heretofore been obtained from natural resources by extraction. The RON substance synthetase of the present invention has the function of forming the RON substance from sucrose. The process for producing the RON substance according to the present invention is a process utilizing this enzyme. Since the production of the RON substance can always be performed under certain optimum conditions, the quality of the product can be unified. Moreover, since the purification is simple, the yield is high. Therefore, conspicuous quantitative and qualitative improvements can be attained according to the present invention, and the present invention is very advantageous from the industrial viewpoint.

The present invention will now be described in detail with reference to the following examples that by no means limit the scope of the invention.

EXAMPLE 1

A stab culture liquid of *Leuconostoc mesenteroides* subsp. *dextranicum*, BL-75 (FERM BP-2242) was inoculated into 5 ml of a preculture medium (comprising 2% of sucrose, 0.5% of yeast extract, 0.25% of tryptone and 0.5% of $K_2HPO_4$ and having a pH value of 7.4), and the static culture was carried out at 25° C. for 24 hours. The culture broth was inoculated in 200 ml of a main culture medium (comprising 2% of sucrose, 0.5% of yeast extract, 2% of $K_2HPO_4$, 0.02% of $MgSO_4$, 0.001% of NaCl, 0,001% of $Fe_2(SO_4)_3$ and 0.001% of $MnSO_4$ and having a pH value of 7.4), and the static culture was carried out at 25° C. for 17 hours.

The obtained culture broth was subjected to centrifugal separation under 10,000 G for 15 minutes to obtain a supernatant. The enzyme activity in the supernatant was 0.74 U/ml and the amount of the liquid was 180 ml. The supernatant was concentrated by an ultrafiltration membrane (Amicon hollow fiber®, exclusion molecular weight=10, 000). The concentrate was substituted with 5 mM acetate buffer having a pH value of 5.5. The solution was saturated with toluene, and finally, 80 ml of an enzyme solution having an activity of 2.0 U/ml was obtained.

EXAMPLE 2

To 30 ml of 50 mM acetate buffer having a pH value of 5.5 and containing 20% of sucrose was added 10 ml (20 U) of the enzyme solution obtained in Example 1, and the mixture was stirred and reaction was carried out at 30° C. Since the time required for completion of the reaction was calculated as 7.3 hours from the amounts of the enzyme and sucrose, the reaction was conducted for 9 hours. Stopping of the reaction was effected by gradually adding 33 ml of methanol to the reaction mixture (the final concentration was 45%) with stirring to precipitate the RON substance. The precipitation with methanol was carried out again for purifying the RON substance. The precipitate was dissolved in water and the solution was freeze-dried to obtain 1.20 g of the RON substance in the form of a white powder (the yield was 85% of the theoretical yield).

EXAMPLE 3

To 15 ml of 50 mM acetate buffer having a pH value of 5.5 and containing 20% of sucrose was added 5 ml (10 U) of the enzyme solution obtained in Example 1, and the mixture was stirred and reaction was carried out at 30° C. The reaction time was adjusted to 18 hours. Then, 16 ml of methanol was gradually added to the reaction mixture with stirring (the final concentration was 45%) to precipitate the RON substance. The precipitation with methanol was carried out again to purify the RON substance. The purified RON substance was dissolved in water and the solution was freeze-dried to obtain 1.16 g of the RON substance in the form of a white powder (the yield was 82% of the theoretical yield).

EXAMPLE 4

To 500 ml of the preculture medium used in Example 1 was added 10 ml of the culture broth obtained from the preculture medium used in Example 1, and the static culture was carried out at 25° C. for 24 hours. The culture broth was added into a jar fermentor having a volume of 30 l, which was charged with 25 l of the main culture medium used in Example 1, and the main culture was carried out at 25° C. for 20 hours with gengle stirring. The obtained culture broth was subjected to centrifugal separation under 13,000 G at a flow rate of 60 l/hr by a continuous centifugal separator to obtain 20 l of a crude enzyme solution having an activity of 0.7 U/ml.

EXAMPLE 5

In 5 l (3500 U) of the crude enzyme solution 500 g of sucrose was dissolved with stirring, and reaction was carried out at 30° C. for 17 hours. After the reaction, 4 l of methanol was gradually added to the reaction mixture with stirring (the final concentration was 45%) to precipitate the RON substance. The formed precipitate was subjected to the precipitation with methanol again, and the purified RON substance was dissolved in water and the solution was spray-dried to obtain 174 g of the RON substance in the form of a white powder (the yield was 74% of the theoretical yield).

EXAMPLE 6

The procedures of Example 1 were repeated in the same manner except that *Leuconostoc mesenteroides* subsp. *dextranicum* 46-1 (FERM BP-2670) was used instead of *Leuconostoc mesenteroides* subsp. *dextranicum*, BL-75 (FERM BP-2242), whereby 70 ml of an enzyme solution having an activity of 2.0 U/ml was obtained.

EXAMPLE 7

The procedures of Example 1 were repeated in the same manner except that *Leuconostoc mesenteroides* subsp. *dextranicum* NCFB 517 (FERM BP-2711) was used instead of *Leuconostoc mesenteroides* subsp. *dextranicum* BL-75 (FERM BP-2242), whereby 30 ml of an enzyme solution having an activity of 2.0 U/ml was obtained.

EXAMPLE 8

The procedures of Example 1 were repeated in the same manner except that *Leuconostoc mesenteroides* subsp. *dextranicum* NCFB 531 (FERM BP-2712) was used instead of *Leuconostoc mesenteroides* subsp. *dextranicum* BL-75 (FERM BP-2242), whereby 45 ml of an enzyme liquid having an activity of 2.0 U/ml was obtained.

EXAMPLE 9

The procedures of Example 1 were repeated in the same manner except that *Leuconostoc mesenteroides* subsp. *dextranicum* ATCC 1956 was used instead of *Leuconostoc mesenteroides* subsp. *dextranicum* BL-75 (FERM BP-2242), whereby 50 ml of an enzyme solution having an activity of 2.0 U/ml was obtained.

EXAMPLE 10

The procedures of Example 1 were repeated in the same manner except that *Leuconostoc mesenteroides* subsp. *dextranicum* NCFB861 (FERM BP-2713) was used instead of *Leuconostoc mesenteroides* subsp. *dextranicum* BL-75, whereby 30 ml of an enzyme solution having an activity of 2.0 U/ml was obtained.

EXAMPLE 11

The procedures of Example 1 were repeated in the same manner except that *Leuconostoc mesenteroides* subsp. *dextranicum* NCFB 864 (FERM BP-2714) was used instead of *Leuconostoc mesenteroides* subsp. *dextranicum* BL-75 (FERM BP-2242), whereby 30 ml of an enzyme solution having an activity of 2.0 U/ml was obtained.

EXAMPLE 12

The procedures of Example 1 were repeated in the same manner except that *Leuconostoc mesenteroides* subsp. *dextranicum* IFO 3349 was used instead of *Leuconostoc mesenteroides* subsp. *dextranicum* BL-75, whereby 45 ml of an enzyme solution having an activity of 2.0 U/ml was obtained.

EXAMPLE 13

The procedures of Example 2 were repeated by using the enzyme solution obtained in example 6 to obtain 1.18 g of the RON substance.

EXAMPLE 14

The enzyme solution obtained in Example 7 was diluted 2 times, and the procedures of Example 2 were repeated by using the dilution to obtain 1.20 g of the RON substance.

EXAMPLE 15

The procedures of Example 2 were repeated using the enzyme solution obtained in Example 8 to obtain 1.17 g of the RON substance.

EXAMPLE 16

The procedures of Example 2 were repeated using the enzyme solution obtained in Example 9 to obtain 1.18 g of the RON substance.

EXAMPLE 17

The procedures of Example 2 were repeated using the enzyme solution obtained in Example 10 to obtain 1.10 g of the RON substance.

EXAMPLE 18

The procedures of Example 2 were repeated using the enzyme solution obtained in Example 11 to obtain 1.13 g of the RON substance.

EXAMPLE 19

The procedures of Example 2 were repeated using the enzyme solution obtained in Example 12 to obtain 1.21 g of the RON substance.

EXAMPLE 20

To 1 g of the white powder of the RON substance obtained in Example 2 was added 100 ml of a sulfuric acid-formic acid mixture solution having a concentration of 2%, and the hydrolysis was carried out at 60° C. for 4 hours. Barium carbonate was added to the hydrolyzate solution to effect neutralization and the solution was subjected to centrifugal separation to obtain a supernatant. A half of the obtained supernatant was subjected to a gel filtration with a column of sepharose CL-2B® to obtain fraction $F_1$ (having a molecular weight higher than 20,000,000 daltons) eluted in the void volume and fraction $F_2$ having an intermediate molecular weight of about 1,000,000 daltons. The remaining half of the supernatant was applied on Sephadex® G-200 to obtain fractions $F_3$ and $F_4$ having intermediate molecular weights of about 100,000 daltons and about 10,000 daltons, respectively. These fractions were freeze-dried to obtain 200 mg, 160 mg, 150 mg and 120 mg of white powders of $F_1$, $F_2$, $F_3$ and $F_4$, respectively.

The biological activities of these fractions are described below.

(1) Antitumor Activity

The activity against syngeneic Meth-A tumor, attained by the oral administration at a dose of 30 mg/kg, was as shown in Table VII.

TABLE VII

| Fraction | Average Tumor Weight (g) | Inhibition Ratio (%) |
|---|---|---|
| Control (saline) | 9.02 | — |
| $F_1$ | 4.51 | 50 |
| $F_2$ | 4.51 | 50 |
| $F_3$ | 5.14 | 43 |
| $F_4$ | 5.32 | 41 |

(2) Immunomodulating Activity (a) Carbon Clearance Test (CCT)

The effect attained by the intraperitoneal administration at a dose of 30 mg/kg on tumor bearing mice was as shown in Table VIII.

TABLE VIII

| Fraction | Phagocytic Index | Relative Value (%) |
|---|---|---|
| control (saline) | $115 \times 10^{-3}$ | 100 |
| $F_1$ | $164 \times 10^{-3}$ | 143 |
| $F_2$ | $155 \times 10^{-3}$ | 135 |
| $F_3$ | $155 \times 10^{-3}$ | 130 |
| $F_4$ | $141 \times 10^{-3}$ | 123 |

(b) Plaque-Forming Cell Test (PFC)

The results obtained when the sensitization was carried out on normal mice with sheep erythrocytes on the 4th days after the intraperitoneal administration at a dose of 30 mg/kg was as shown in Table IX.

TABLE IX

| Fraction | Number of Plaques per Spleen | Relative Value (%) |
| --- | --- | --- |
| control (saline) | $3.8 \times 10^4$ | 100 |
| $F_1$ | $7.6 \times 10^4$ | 200 |
| $F_2$ | $7.7 \times 10^4$ | 203 |
| $F_3$ | $7.1 \times 10^4$ | 187 |
| $F_4$ | $6.5 \times 10^4$ | 171 |

(c) Delayed Type Hypersensitivity Reaction (DHR)

The effect obtained by the intraperitoneal administration at a dose of 30 mg/kg on tumor-bearing mice was as shown in Table X.

TABLE X

| Fraction | Increase of Ear Thickness (μm) | Relative Value (%) |
| --- | --- | --- |
| control (saline) | 11.0 | 100 |
| $F_1$ | 22.9 | 208 |
| $F_2$ | 23.3 | 212 |
| $F_3$ | 20.9 | 190 |
| $F_4$ | 19.8 | 180 |

(3) Host Defense Activity against Infectious Diseases

The defense activity attained by the subcutaneous administration at a dose of 30 mg/kg one day before the infection was as shown in Table XI.

TABLE XI

| | E. coli. | | List. mono. | |
| --- | --- | --- | --- | --- |
| Fraction | Number of Survival Mice | Protective Effect (%) | Number of Survival Mice | Protective Effect (%) |
| control (saline) | 0 | — | 0 | — |
| $F_1$ | 19 | 95 | 12 | 60 |
| $F_2$ | 19 | 95 | 10 | 50 |
| $F_3$ | 18 | 90 | 8 | 40 |
| $F_4$ | 17 | 85 | 8 | 40 |

The defense effect attained by the subcutaneous administration at a dose of 30 mg/kg one day after the infection was as shown in Table XII.

TABLE XII

| | E. coli. | | List. mono. | |
| --- | --- | --- | --- | --- |
| Fraction | Number of Survival Mice | Protective Effect (%) | Number of Survival Mice | Protective Effect (%) |
| control (saline) | 0 | — | 0 | — |
| $F_1$ | 16 | 80 | 10 | 50 |
| $F_2$ | 14 | 70 | 9 | 45 |
| $F_3$ | 14 | 70 | 8 | 40 |
| $F_4$ | 12 | 60 | 7 | 35 |

From the foregoing results, it was found that even if the macromolecular RON substance of the present invention is hydrolyzed to a fraction having a molecular weight of about 10,000 daltons, various biological activities of the fraction can be maintained at the levels comparable to those of the original macromolecular RON substance.

When the toxicities of the molecular weight-reduced fractions of the RON substance were examined using mice, in case of the oral administration, no toxicity was observed in any of the fractions as in the original macromolecular RON substance, and in case of the intravenous injection, although $LD_{50}$ of the original macromolecular RON substance was 300 mg/kg, the toxicity decreased with decrease of the molecular weight and $LD_{50}$ of fraction $F_4$ having a molecular weight of about 10,000 daltons was larger than 1 g/kg and no toxicity was observed at all.

In view of the fact that the molecular weight-reduced products of macromolecular RON substance has various biological activities without showing any toxicity at all, it is considered that these substance will be advantageously used as an injection drug or the like.

What is claimed is:

1. A process for producing a polysaccharide RON substance which comprises (a) contacting sucrose with a polysaccharide RON substance synthetase derived from a microorganism having a capacity of producing the polysaccharide RON substance, the microorganism belonging to the genus Leuconostoc and being at least one strain of *Leuconostoc mesenteroides* subsp. *dextranicum*, said strain selected from the group consisting of strain BL-75 (FERM BP-2242), strain NCFB 517 (FERM BP-2711), strain NCFB 531 (FERM BP-2712), strain NCFB 861 (FERM BP-2713), strain NCBF 864 (FERM BP-2714), strain 46-1 (FERM BP-2670), and mutants thereof, to form the polysaccharide RON substance having the following properties:

(1) form: the substance is a white amorphous powder;

(2) solubility: the substance is soluble in water, but the solution becomes milky white and viscous when the concentration is elevated; the substance is soluble in formamide and dimethylsulfoxide, but the substance is insoluble in alcohols, acetone, benzene, ethyl acetate, hexane, chloroform and carbon tetrachloride;

(3) pH of aqueous solution: the aqueous solution is neutral or weakly acidic;

(4) constituent saccharide: the substance comprises solely glucose;

(5) elementary analysis values: the substance comprises 44.0 to 45.0% C and 6.1 to 6.3% of H;

(6) structure: the substance is an α-1,6-glucan and comprises a small amount of 3,6-branched side chains;

(7) proteins: the substance contains almost no proteins;

(8) molecular weight: the substance does not permeate through a dialysis membrane and the molecular weight is considered to be higher than 10,000 daltons;

(9) specific rotation: formamide);

(10) color reaction: the substance is positive to an anthrone sulfuric acid reaction and a phenol sulfuric acid reaction, but negative to a biurette reaction, the Lowry-Folin reaction, the Elson-Morgan reaction and an iodine reaction;

(11) ultraviolet absorption spectrum: the substance has no characteristic absorption;

(12) infrared absorption spectrum: the substance shows a characteristic absorption of α-glucan;

(13) $^{13}$C-NMR spectrum: the substance shows an absorption having characteristic chemical shift values of α-1, 6-glucan in the main signals; and

(14) biological activity: the substance has an antitumor activity against a transplantable tumor in mice, said transplantable tumor being syngeneic tumor Meth A;

and (b) collecting said substance.

2. The process for producing the polysaccharide RON substance according to claim 1, wherein the microorganism having a capacity of producing the polysaccharide RON substance is *Leuconostoc mesenteroides* subsp. *dextranicum*, strain BL-75 (FERM BP-2242) or strain 46-1 (FERM BP-2670).

3. The process for producing the polysaccharide RON substance according to claim 1, wherein the sucrose is in a form of white refined sugar, molasses or reagent grade sucrose.

4. The process for producing the polysaccharide RON substance according to claim 3, wherein the synthetase is in a concentration of 0.2 to 2 U/ml.

5. The process for producing the polysaccharide RON substance according to claim 3, wherein the synthetase is in a concentration of 0.5 to 1 U/ml.

6. The process for producing the polysaccharide RON substance according to claim 5, wherein the sucrose is in a concentration of 5 to 30%.

7. A process for producing a polysaccharide RON substance which comprises (a) contacting sucrose with a polysaccharide RON substance synthetase to form the polysaccharide RON substance having the following properties:

(1) form: the substance is a white amorphous powder;

(2) solubility: the substance is soluble in water, the substance is soluble in formamide and dimethylsulfoxide, but the substance is insoluble in alcohols, acetone, benzene, ethyl acetate, hexane, chloroform and carbon tetrachloride;

(3) pH of aqueous solution: the aqueous solution is neutral or weakly acidic;

(4) constituent saccharide: the substance comprises solely glucose;

(5) elementary analysis values: the substance comprises 44.0 to 45.0% of C and 6.1 to 6.3% of H;

(6) structure: the substance is an α-1,6-glucan and comprises a small amount of 3,6-branched side chains;

(7) proteins: the substance comprises almost no proteins;

(8) molecular weight: the substance does not permeate through a dialysis membrane and the molecular weight is considered to be higher than 10,000 daltons;

(9) specific rotation: $(\alpha)_D^{25}=+190°\sim+220°$ (C=0.5, formamide);

(10) color reaction: the substance is positive to an anthrone sulfuric acid reaction and a phenol sulfuric acid reaction, but negative to a biurette reaction, the Lowry-Folin reaction, the Elson-Morgan reaction and an iodine reaction;

(11) ultraviolet absorption spectrum: the substance has no characteristic absorption;

(12) infrared absorption spectrum: the substance shows a characteristic absorption of α-glucan;

(13) $^{13}$C-NMR spectrum: the substance shows an absorption characteristic of chemical shift values of α-1,6-glucan in the main signals; and

(14) biological activity: the substance has an antitumor activity against a transplantable tumor in mice, said tumor being syngeneic tumor Meth A;

and (b) collecting said substance.

8. The process for producing a polysaccharide RON substance according to claim 10, wherein the RON substance synthetase is a polysaccharide RON substance synthetase having the following properties:

(a) action: the enzyme decomposes 1 mol of sucrose to form 1 mol of fructose, and simultaneously, the enzyme transfers the glucose portion to the polysaccharide RON substance acting as the receptor;

(b) optimum pH: the optimum pH value is about 5.5;

(c) stable pH range: the enzyme is stable in the pH range of from 4.5 to 7.0;

(d) substrate specificity: formation of the biologically active polysaccharide RON substance from glucose, fructose, maltose and isomaltose is not observed, but the enzyme reacts only with sucrose to form the biologically active polysaccharide RON substance;

(e) optimum temperature: the optimum temperature is about 40° C.; and (f) stable temperature range: the enzyme is stable at a temperature lower than 40° C.

* * * * *